(12) United States Patent
Ong et al.

(10) Patent No.: US 7,413,806 B2
(45) Date of Patent: Aug. 19, 2008

(54) IMPLANT COATINGS

(75) Inventors: Joo L. Ong, San Antonio, TX (US);
Rajiv K. Satsangi, San Antonio, TX (US); Neera Satsangi, San Antonio, TX (US)

(73) Assignee: Board of Regents, The University of Texas System, Austin, TX (US)

( * ) Notice: Subject to any disclaimer, the term of this patent is extended or adjusted under 35 U.S.C. 154(b) by 477 days.

(21) Appl. No.: 10/497,671

(22) PCT Filed: Dec. 17, 2002

(86) PCT No.: PCT/US02/40172

§ 371 (c)(1),
(2), (4) Date: Jan. 13, 2005

(87) PCT Pub. No.: WO03/053218

PCT Pub. Date: Jul. 3, 2003

(65) Prior Publication Data

US 2005/0123765 A1 Jun. 9, 2005

(51) Int. Cl.
*A61F 2/28* (2006.01)
*B32B 15/04* (2006.01)
*B32B 9/00* (2006.01)

(52) U.S. Cl. .............. 428/411.1; 428/420; 428/457; 623/23.57

(58) Field of Classification Search .......... 428/411.1, 428/420, 457; 623/23.57
See application file for complete search history.

(56) References Cited

U.S. PATENT DOCUMENTS

| | | | |
|---|---|---|---|
| 2,989,455 A | 6/1961 | Neugebauer et al. | |
| 3,715,293 A | 2/1973 | Sandner et al. | |
| 4,308,400 A | 12/1981 | Felder et al. | |
| 4,459,193 A | 7/1984 | Ratcliffe et al. | |
| 4,818,559 A * | 4/1989 | Hama et al. | 427/2.27 |
| 5,342,621 A | 8/1994 | Eury | |
| 5,711,959 A * | 1/1998 | Kohler et al. | 424/423 |
| 5,721,292 A | 2/1998 | Leppard et al. | |
| 2003/0028204 A1* | 2/2003 | Li et al. | 606/152 |

FOREIGN PATENT DOCUMENTS

WO WO 01/15752 A1 3/2001

OTHER PUBLICATIONS

A.L. Boskey and A.S. Posner, "Optimal Condition for Ca-acidic Phospholipid-$PO_4$ Formation" *Calcified Tissue International* 34:S1-S7 (1982).

(Continued)

*Primary Examiner*—Ramsey Zacharia
(74) *Attorney, Agent, or Firm*—Meyertons, Hood, Kivlin, Kowert & Goetzel, P.C.; Eric B. Meyertons

(57) ABSTRACT

Implants may be coated with a biocompatible coating to improve the biocompatibility of the implant. The biocompatible coating may include a bone growth promoting compound. Such compounds include, but are not limited to, phospholipids, bone morphogenetic proteins, or combinations thereof. The bone growth promoting compound may enhance the rate of bone growth proximate to the implant and the integration of the implant into the surrounding bone.

7 Claims, 9 Drawing Sheets

OTHER PUBLICATIONS

P. Ducheyne et al., "Calcium Phosphate Ceramic Coatings on Porous Titanium: Effect of Structure and Composition on Electrophoretic Deposition, Vacuum Sintering, and In Vitro Dissolution" *Biomaterials* 11:244-254 (1990).

A. Nanci et al., "Chemical Modification of Titanium Surfaces for Covalent Attachment of Biological Molecules" *Journal of Biomedical Material Research* 40:324-335 (1998).

B.D. Boyan-Salyers and A.L. Boskey, "Relationship Between Proteolipids and Calcium-Phospholipid-Phosphate Complexes in *Bacterionema Matruchotii* Calcification" *Calcified Tissue International* 30:167-174 (1980).

S. Ong et al., "Phospholipid Immobilization on Solid Surfaces" *Analytical Chemistry* 66:782-792 (1994).

S.F. Yang et al., "Transphosphatidylation by Phospholipadase D" *The Journal of Biological Chemistry* 242(3):477-484 (1967).

Oh et al. "Conjugation of drug to poly(dl-lactic-co-glycolic acid) for Controlled Release from Biodegradable Microsphere" *J. Controlled Release*, 57:269-280, 1999.

Thomas et al. "Symmetrical, Biodegradable Cross-linker Based on Lactic or Glycolic Acid: Preparation and Hydrolysis Rate Studied" *Book of Abstracts, 219th ACS National Meeting, San Francisco, CA*, Mar. 26-30, 2000, ORGN-394.

Satsangi et al. "A Novel Method for the Analysis of Platelet Activating Factor: Direct Derivatization of Glycerophospholipids", *J. Lipid Res.* 30, 929-937, 1989.

International Search Report for International application No. PCT/US02/40172 (Our Ref. No. 5660-00302) mailed Apr. 24, 2003.

"Biomedical Materials", *Chemistry for Health* Royal Society for Chemistry, Briefing Paper 2, Mar. 1999.

* cited by examiner

Phospholipase D

R³-OH

↓

+

↓

Protein-NH

IMPLANT COATINGS

BACKGROUND OF THE INVENTION

1. Field of the Invention

The invention generally relates to coating materials for implants that are used as bone or dental substitutes. More specifically, the invention generally relates to coating materials that include a bone growth promoting agent.

2. Description of the Relevant Art

A goal of the placement of an endosseous implant is to achieve osseointegration of bone with the implant. "Osseointegration" is herein defined as the direct contact of the loaded implant material with living bone. Previously, materials were sought which would act as inert substances, usually eliciting a fibrous encapsulation around them. Osseointegration cannot occur, however, when a fibrous layer is present. It is believed that the biological response of bone is not inertness towards foreign materials, but rather integration of the material with the bone as if it were the part of the body.

In general, only the surface of an implant is in direct contact with host tissue. Thus, an implant surface may play a role in determining biocompatibility of the implant with the surrounding bone. Modifications of the implant surface may be employed as a means of controlling cellular responses to biomaterial surfaces and the process of induction of bone generation.

Plasma sprayed hydroxyapatite ("HA") has been applied to titanium implants to enhance osteoconduction. The rationale for coating implants with HA grew out of the desire to combine the bioactivity of HA with the strength of titanium. Studies have demonstrated that dental and orthopedic implants coated with plasma sprayed HA promote greater direct bone attachment and higher interfacial strength compared to the uncoated titanium implants. The performance of HA coated implants is attributed to more rapid osseointegration and the development of increased interfacial strength that results from the early skeletal attachment and increased bone contact with the implant surface. In vivo research indicates that HA coated implants are biocompatible and may perform better than non-coated titanium implants.

HA coatings have a number of problems, including variation in bond strength at the coating-metal interface, variation in coating thickness among vendors, variation in structural and chemical properties, and nonuniformity in coating density. These problems have made it unclear whether or not plasma sprayed HA coatings are actually beneficial to implant success. It appears, however, that these problems reflect shortcomings inherent in the plasma spray technology rather than the rationale for the coating.

There are no accepted standards for plasma spraying HA on implants, and studies indicate differences among plasma sprayed HA coatings. Conflicting animal and clinical observations have been reported as a result of variable coating quality. It has been shown that the coating processes employed by manufacturers result in different surfaces, chemistries, and structures of plasma sprayed HA coatings. These differences may alter the cascade of cellular activity and host tissue responses.

Clinical failures of plasma sprayed HA coated implants have been observed to occur due to premature degradation or delamination at the HA-metal interface, indicating a weak bond at the coating-metal interface compared to bone-HA interface. Failures have been related to the dissolution of the coatings as well as the weak coating-substrate interface. Dissolution of the coatings is dependent not only on the crystallinity of the surface, but also on the porosity of the coating. During plasma spraying, there is porosity present between, as well as within, the laminar structure of the semi-molten particles that is not squeezed out on impact with the substrate. A high porosity level tends to lead to a higher dissolution rate of the coating.

Besides implant failure caused by dissolution of the coatings, failure of implants is also the result of delamination of the coatings at the coating-implant interface. The delamination of the coatings at the coating-implant interface may be related to the thickness of the applied layer. Currently, the HA coatings of commercial implants are fabricated by a modified plasma spray process that produces a thick coating. However, a report on the measurement of the HA coating thickness revealed inconsistent coating thickness among different vendors. Some coatings were observed to have significantly expanded when compared to the coating thickness prior to implantation, indicating the presence of fluid behind and within the coatings. Such coating expansion was suggested to mark the beginning of coating breakup leading to failure. Finally, it has been shown that thin HA coatings (2 μm) have a significantly greater coating-metal interfacial strength than commercially available thick (70 μm) plasma sprayed HA.

SUMMARY OF THE INVENTION

In an embodiment, implants may be coated with a biocompatible coating to improve the biocompatibility of the implant. The biocompatible coating may include a bone growth promoting compound. Such compounds include, but are not limited to, phospholipids, bone morphogenetic proteins, or combinations thereof. The coating is applied to the implant The coating may be adsorbed onto the implant, polymerized to form a coating surrounding a portion of the implant, or covalently coupled to the implant through a linker group. The bone growth promoting compound may enhance the rate of bone growth proximate to the implant. The bone growth promoting compound may also enhance the integration of the implant into the surrounding bone. The implants described herein may be used in orthopedic applications and dental applications.

In an embodiment, an implant may be coated with a calcium-phospholipid-phosphate complex. Phospholipids are compounds that include a glyceryl backbone. The glyceryl backbone includes three oxygen groups. The first and second oxygen groups may be derivatized to an ester or an ether. The third oxygen may be derivatized as a phosphodiester group. The most common phospholipids include those derivatized at a first position with a long chain fatty acid (e.g., acid groups having between 6 to 24 carbon atoms) or a long chain fatty ether; at a second position, with an acetyl or a long chain fatty acid, and a phosphodiester group at the third position. The implant may be formed from titanium, a titanium alloy (e.g., titanium-vanadium-aluminum alloy), surgical grade stainless steel, nickel-chromium alloys, nickel-chromium-cobalt alloys or a biocompatible polymeric material. It is believed that the calcium-phospholipid-phosphate complex will enhance the rate of bone growth around the implant. This may lead to better and faster integration of the implant into surrounding bones.

In an embodiment, an implant may be coated by contacting a coating composition that includes a calcium-phospholipid-phosphate complex with a surface of the implant. The implant may be immersed in a solution of the calcium-phospholipid-phosphate complex. The implant may be contacted with the coating composition for a time of up to about 24 hours. In some embodiments, the coating composition is an organic solution of the calcium-phospholipid-phosphate complex. A surface of the implant may be contacted with the coating composition to form a coating layer. After removal from the coating composition, the implant may be irradiated with ultraviolet light or gamma radiation to keep the implant sterilized while the coating composition is dried. While the implant is in contact with the coating composition, a portion of the calcium-phospholipid-phosphate complex may be adsorbed by the implant surface. The non-adsorbed portion of the implant may be washed from the implant surface. The implant may be again sterilized prior to usage by irradiating the coated implant with ultraviolet light.

In another embodiment, an implant may be coated with a polymeric coating that includes calcium-phospholipid-phosphate repeat units. The coating may be formed from a phospholipid acrylate which is applied to the implant surface and cured to form the polymeric coating. The implant may be formed from titanium, a titanium alloy (e.g., titanium-vanadium-aluminum alloy), surgical grade stainless steel, nickel-chromium alloys, nickel-chromium-cobalt alloys, or a biocompatible polymeric material. It is believed that the calcium-phospholipid-phosphate polymeric coating will enhance the rate of bone growth around the implant. This may lead to better and faster integration of the implant into surrounding bones.

In an embodiment, an implant may be coated by applying a coating composition that includes a phospholipid acrylate and a photoinitiator with a surface of the implant The implant may be irradiated using activating light to polymerize the phospholipid acrylates into a polymeric coating. The formed polymeric coating may include phospholipid repeat units so that all bioactive sites of phospholipid structures remain unaffected. The phospholipid repeat units may be converted to calcium-phospholipid-phosphates by reaction of the polymerized coating layer with calcium chloride and ammonium hydrogen phosphate.

In another embodiment, an implant may be coated with a calcium-phospholipid-phosphate coating layer that is covalently coupled to the implant surface though a linker. The linker group includes a reactive group at a distal end of the linker group which allows coupling of the phospholipid to the implant The linker may be formed from a biodegradable material. The coating may be formed from a phospholipid having a linking group which is coupled to an oxidized implant surface to form the implant coating. The implant may be formed from titanium, a titanium alloy (e.g., titanium-vanadium-aluminum alloy), surgical grade stainless steel, nickel-chromium alloys, nickel-chromium-cobalt alloys, or a biocompatible polymeric material. The implants may be oxidized to provide surface hydroxyl groups that allow the coupling of calcium-phospholipid-phosphate groups to the implant surface through a linker. It is believed that the calcium-phospholipid-phosphate polymeric coating will enhance the rate of bone growth around the implant. This may lead to better and faster integration of the implant into surrounding bones.

BRIEF DESCRIPTION OF THE DRAWINGS

Other objects and advantages of the invention will become apparent upon reading the following detailed description and upon reference to the accompanying drawings in which.

Figure 1:
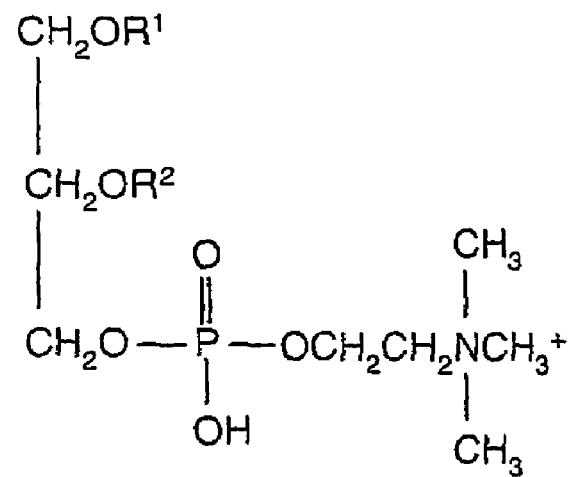
FIG. 1 depicts a transphosphatidylation reaction of a phospholipid.
Figure 1:
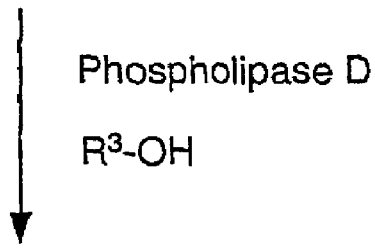
Figure 1:
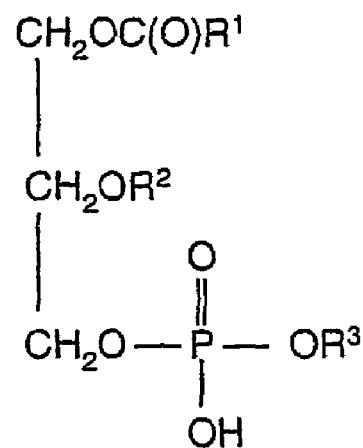

While the invention is susceptible to various modifications and alternative forms, specific embodiments thereof are shown by way of example in the drawing and will herein be described in detail. It should be understood, however, that the drawings and detailed description thereto are not intended to limit the invention to the particular form disclosed, but on the contrary, the intention is to cover all modifications, equivalents, and alternatives falling within the spirit and scope of the present invention as defined by the appended claims.

DETAILED DESCRIPTION OF THE INVENTION

Calcium-phospholipid-phosphate Adsorbed Coatings

In an embodiment, an implant may be coated with a calcium-phospholipid-phosphate complex. The phospholipid portion of the coating has the general structure (1) depicted below:

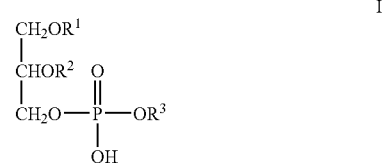

where $R^1$ and $R^2$ are each independently H, $C_1$-$C_{24}$ alkyl, $C_2$-$C_{24}$ alkenyl, or $C(O)R^4$, where $R^4$ is $C_1$-$C_{24}$ alkyl or $C_2$-$C_{24}$ alkenyl.

$R^3$ includes residues attached to the phosphate group. $R^3$ includes glycerol [$CH_2$—$CH(OH)$—$CH_2(OH)$];
choline [—$CH_2$—$CH_2$—$N(CH_3)_3^+$]; ethanolamine [—$CH_2$—$CH_2$—$NH_3^+$]; monomethylethanolamine [—$CH_2$—$CH_2$—$N(CH_3)H_2^+$];
dimethylethanolamine [—$CH_2$—$CH_2$—$N(CH_3)_2H^+$];
serine [—$CH_2$—$CH(NH_3)^+$—$CO_2^-$];
a carbohydrate

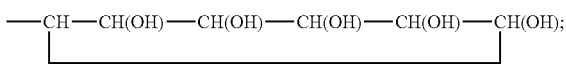

or
a diphosphatidylglycerol [—$CH_2$—$CH(OH)$—$CH_2$—O—$PO_3$—$CH_2$—$CH(OC(O)R^5)$—$CH_2$—$OC(O)R^6$], where $R^5$ and $R^6$ are each independently $C_1$-$C_{24}$ alkyl or $C_2$-$C_{24}$ alkenyl. These residues are further depicted below.

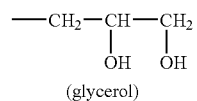

(glycerol)

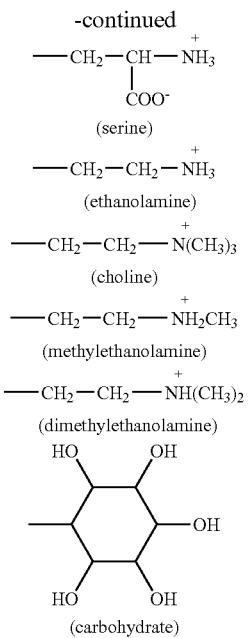

(serine)
(ethanolamine)
(choline)
(methylethanolamine)
(dimethylethanolamine)
(carbohydrate)

The most common carbohydrate residue coupled to the phosphate group is the inositol group.

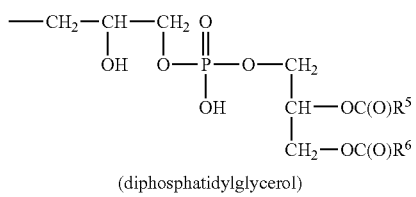

(diphosphatidylglycerol)

$R^1$ and $R^2$ of structure I may include carboxylic acid groups bound through the carbonyl group to the hydroxyl of the glyceral backbone. Examples of carboxylic acid groups include, but are not limited to the following (trivial names are in parenthesis): acetic, propanoic (propionic), butanoic (butyric), pentanoic (valeric), hexanoic (caproic), heptanoic, octanoic (caprylic), decanoic (capric), dodecanoic (lauric), tetradecanoic (myristic), hexadecanoic (palmitic), octadecanoic (stearic), eicosanoic (arachidic), docosanoic (behenic), 9-hexadecenoic (palmitoleic), 6-octadecenoic (petroselinic), 9-octadecenoic (oleic), 11-octadecenoic, 13-docosenoic, 15-tetracosenoic, 9,12-octadecadienoic (linoleic), 6,9,12-octadecatrienoic (gamma-linolenic), 9,12,15-octadecatrienoic (alpha-linolenic), 5,8,11,14-eicosatetraenoic, 5,8,11,14,17-eicosapentaenoic, and 4,7,10,13,16,19-docosahexaenoic.

Many phospholipids are readily available from commercial sources (e.g., Sigma-Aldrich, Milwaukee, Wis.). Phospholipids may be obtained from natural sources or synthesized using known techniques. The most common naturally occurring and commercially available phospholipids are the phosphatidylcholines. Phosphatidylcholines have the general structure (II) depicted below. Phosphatidylcholines are phospholipids that include a choline residue bound to the phosphate group.

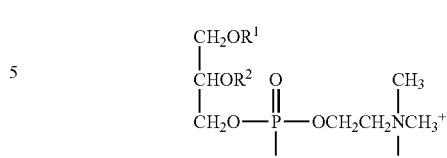

Phosphatidylcholines may be converted to other phospholipids using a transphosphatidylation reaction. A transphosphatidylation reaction is depicted in FIG. 1. Generally a phosphatidylcholine is reacted with an alcohol in the presence of a transphosphatidylation enzyme. The alcohol replaces the choline of the phosphatidylcholine to produce a new phospholipid with the alcohol incorporated into the phosphodiester group. Alcohols that may be used include, but are not limited to glycerol, ethanolamine, serine and carbohydrates. In one embodiment, the enzyme phospholipase D is used to catalyze transphosphatidylation of choline to serine. In FIG. 1, $R^1$ and $R^2$ are each independently H, $C_1$-$C_{24}$ alkyl, $C_2$-$C_{24}$ alkenyl, or $C(O)R^4$, where $R^4$ is $C_1$-$C_{24}$ alkyl or $C_2$-$C_{24}$ alkenyl. $R^3$ is glycerol, ethanolamine, monomethylethanolamine, dimethylethanolamine, serine, a carbohydrate, or a diphosphatidylglycerol.

In a general procedure, an alcohol is placed with a transphosphatidylation enzyme (e.g., phospholipase D) in a buffer solution (e.g., acetate buffer). The buffer solution may also include calcium chloride. The solution may be buffered to a pH to obtain the maximum activity of the transphosphatidylation enzyme. For the transphosphatidylation enzyme phospholipase D the optimum activity is obtained at a pH between about 5 and about 6. A phosphatidylcholine, dissolved in a suitable organic solvent (e.g., diethyl ether) are added to the buffer solution and the mixture may be allowed to react for an appropriate amount of time at a temperature above room temperature. Typically the reaction is performed at about 37° C. The reaction time may be determined based on the enzyme used and the concentration of the reaction. Generally, 1 unit of enzyme reacts with 1 mmol of a substrate in about 1 hour. Based on the concentration of the substrate, the required reaction time may be calculated. During the reaction the added alcohol exchanges with the choline group of the phosphatidylcholine. The temperature and the amount of time may depend on the activity of the enzyme and the relative amounts of enzyme and substrate. After the reaction is completed hydrochloric acid may be added to stop the reaction. The obtained phospholipid product may be separated from the reaction mixture and purified. Typical contaminates may include unreacted phosphatidylcholine and hydrolyzed phosphatidylcholine. Purification may be accomplished by chromatography. Further details regarding a transphosphatidylation process may be found in the paper by Yang et al. "Transphosphatidylation by Phospholipase D" *J. Biol. Chem.*, 242(3), pp. 477-484, 1967, which is incorporated herein by reference.

Listed below are exemplary compounds that may be synthesized from this process. All of the below compounds may be synthesized from the reaction of the corresponding phosphatidylcholine with a transphosphatidylation enzyme (e.g., phospholipase D) in the presence of serine.

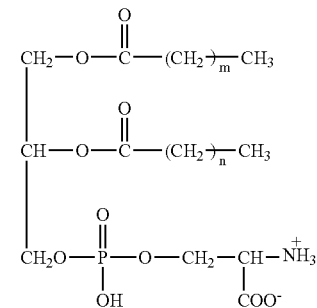

n,m=8: 1,2-didecoyl-sn-glycerol-3-phosphatidyl-L-serine
n,m=10: 1,2-didodecoyl-sn-glycerol-3-phosphatidyl-L-serine
n,m=12: 1,2-dimiristoyl-sn-glycerol-3-phosphatidyl-L-serine;
n,m=14: 1,2-dipalmitoyl-sn-glycerol-3-phosphatidyl-L-serine;
n,m=16: 1,2-distearoyl-sn-glycerol-3-phosphatidyl-L-serine;

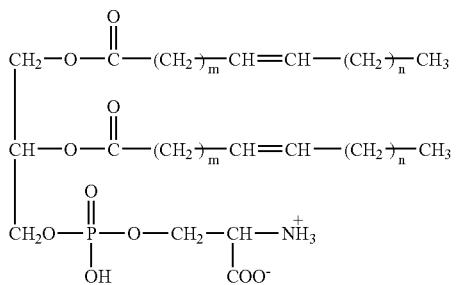

n,m=6: 1,2-dipalmitoleoyl-sn-glycerol-3-phosphatidyl-L-serine
n,m=7: 1,2-dioleoyl-sn-glycerol-3-phosphatidyl-L-serine;

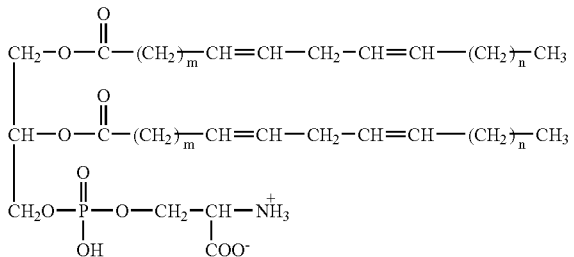

m=7, n=4: 1,2-dilinoleoyl-sn-glycerol-3-phosphatidyl-L-serine;

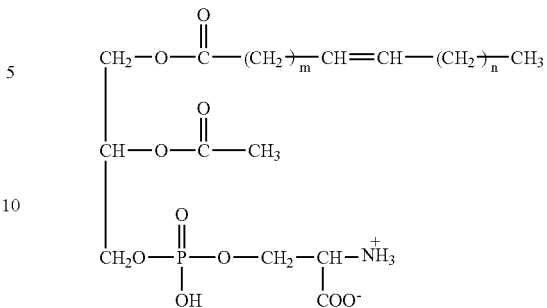

n,m=6: 1-dipalmitoleoyl, 2-acetyl-sn-glycerol-3-phosphatidyl-L-serine
n,m=7: 1-oleoyl, 2-acetyl-sn-glycerol-3-phosphatidyl-L-serine;

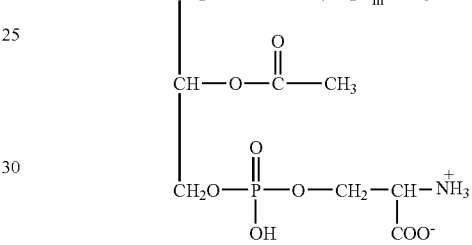

m=14: 1-palmitoyl, 2-acetyl-sn-glycerol-3-phosphatidyl-L-serine;
m=16: 1-stearoyl, 2-acetyl-sn-glycerol-3-phosphatidyl-L-serine.

The obtained phospholipids may be converted to a calcium-phospholipid-phosphate complex. In a general procedure the phospholipid is reacted with calcium chloride ($CaCl_2$) and ammonium hydrogenphosphate (($NH_4)_2HPO_4$). The reaction of the phospholipid with the calcium chloride and the ammonium hydrogenphosphate produces a calcium-phospholipid-phosphate complex. The phospholipid is added to a solution of the $CaCl_2$ and $(NH_4)_2HPO_4$ and sonicated at about 0° C. for about 1 minute. The reaction mixture was then agitated for at least 24 hours at a temperature above 25° C., in some embodiments between about 30° C. and 40° C. An organic solvent mixture (e.g., chloroform-methanol 2:1) is added to the reaction mixture and the solid material removed by centrifugation. The organic solvent layer is washed with dilute hydrochloric acid (e.g., about $10^{-5}$ N HCl) to remove unreacted phospholipid. The formed calcium-phospholipid-phosphate may be recovered from the organic phase using known procedures. Further details may be obtained from the paper by Boskey et al. "Optimal Conditions for Ca-acidic Phospholipid-PO$_4$ Formation, *Calcif. Tissue Intern.* 34, S1-S7, 1982, which is incorporated herein by reference.

A calcium-phospholipid-phosphate complex may be adsorbed onto an implant surface to form a coating on the implant surface. In an embodiment, the implant may be contacted with a coating composition. The coating composition includes a calcium-phospholipid-phosphate complex. In some embodiments, the calcium-phospholipid-phosphate complex is an organic solution of the calcium-phospholipid-phosphate. The implant may be partially or wholly immersed in the coating composition. While the implant is in contact with the coating composition, the implant may be irradiated with ultraviolet light to keep the implant sterilized. As used herein, ultraviolet light includes light having wavelengths between about 100 nm and 400 nm. The implant may be contacted or immersed in the coating composition for up to 24 hours. After being immersed in the coating composition for a time adequate to form a coating layer on the implant, the implant may be removed and the non-adsorbed calcium-phospholipid-phosphate complex washed off using water. The implant may be further sterilized by treating the implant with ultraviolet light for at least 48 hours prior to use.

Implants may be formed from a variety of biocompatible materials. The most common materials include titanium. Titanium alloys may also be used as implant materials. An example of a titanium alloy is an alloy of titanium alloyed with 6% aluminum and 4% vanadium. Other materials such as stainless steel, nickel-chromium alloys, nickel-chromium-cobalt alloys may be used. Implants may also be formed from biocompatible polymeric materials. Examples of polymeric materials include, but are not limited to, ultra high molecular weight polyethylene, polylactic acid, and polyglycolic acid.

Polymeric Phospholipid Coatings

In an embodiment, implant materials may be coated with a polymerized coating that includes calcium-phospholipid-phosphate complexes as repeat units. In one embodiment, the coating material may be formed from a phospholipid acrylate. An example of a phospholipid acrylate is depicted as structure (III) below:

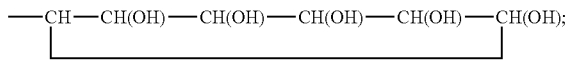

where $R^1$ is H, $C_1$-$C_{24}$ alkyl, $C_2$-$C_{24}$ alkenyl, or $C(O)R^4$,
where $R^4$ is $C_1$-$C_{24}$ alkyl or $C_2$-$C_{24}$ alkenyl;
where $R^2$ is H or CH$_3$;
where $R^3$ includes residues attached to the phosphate group. $R^3$ includes glycerol [CH$_2$—CH(OH)—CH$_2$(OH)]; choline [—CH$_2$—CH$_2$—N(CH$_3$)$_3^+$]; ethanolamine [—CH$_2$—CH$_2$—NH$_3^+$]; serine [—CH$_2$—CH(NH$_3$)$^+$—CO$_2^-$];
a carbohydrate

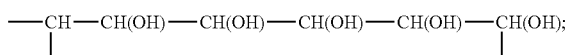

or
a diphosphatidylglycerol [—CH$_2$—CH(OH)—CH$_2$—O—PO$_3$—CH$_2$—CH(OC(O)R$^5$)—CH$_2$—OC(O)R$^6$],
where $R^5$ and $R^6$ are each independently $C_1$-$C_{24}$ alkyl or $C_2$-$C_{24}$ alkenyl.

$R^1$ of structure III may include a carboxylic acid group bound through the carbonyl group to the hydroxyl of the glyceral backbone. Examples of carboxylic acid groups include, but are not limited to the following (trivial names are in parenthesis): acetic, propanoic (propionic), butanoic (butyric), pentanoic (valeric), hexanoic (caproic), heptanoic, octanoic (caprylic), decanoic (capric), dodecanoic (lauric), tetradecanoic (myristic), hexadecanoic (palmitic), octadecanoic (stearic), eicosanoic (arachidic), docosanoic (behenic), 9-hexadecenoic (palmitoleic), 6-octadecenoic (petroselinic), 9-octadecenoic (oleic), 11-octadecenoic, 13-docosenoic, 15-tetracosenoic, 9,12-octadecadienoic (linoleic), 6,9,12-octadecatrienoic (gamma-linolenic), 9,12,15-octadecatrienoic (alpha-linolenic), 5,8,11,14-eicosatetraenoic, 5,8,11,14,17-eicosapentaenoic, and 4,7,10,13,16,19-docosahexaenoic.

Phospholipid acrylates may be formed from a lysophospholipid. Lysophospholipids have the general structure (IV).

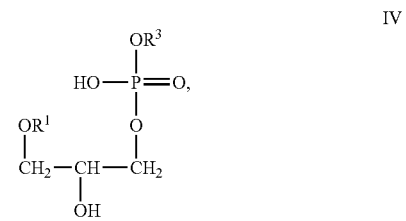

Figure 2:
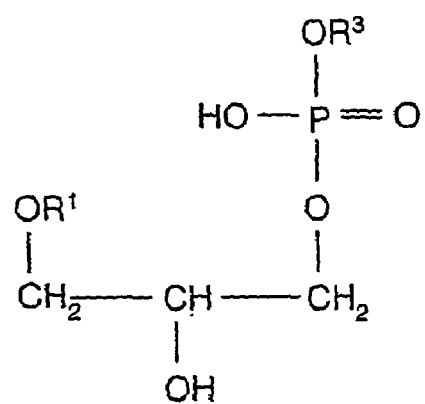
FIG. 2 depicts the synthesis of a phospholipid acrylate from a lysophospholipid.
Figure 2:
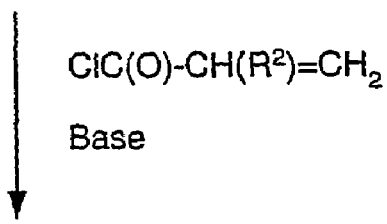
Figure 2:
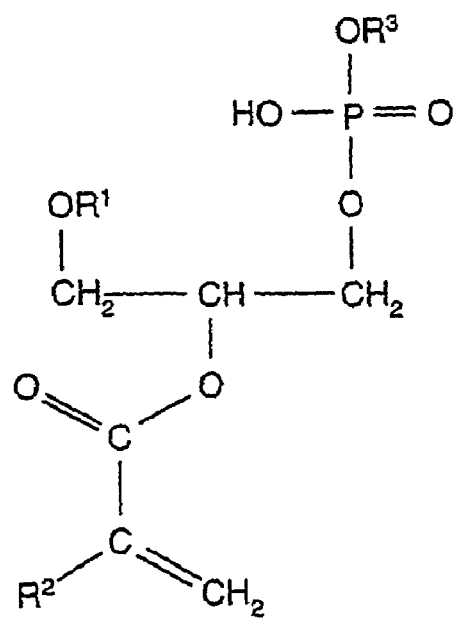

$R^1$ and $R^3$ are the same as described previously for other phospholipids. Lysophospholipids have only one group ($R^1$) coupled to the glyceral backbone. The other hydroxy group (e.g., the hydroxyl at the 2-position) exists as a free hydroxy group. Lysophosphatidylcholines (IV, $R^3$ is choline) are convenient and readily available starting materials for the synthesis of phospholipid acrylates. The general synthesis of phospholipid acrylates is depicted in FIG. 2. The lysophospholipid is reacted with either acryloyl chloride ($R^2$ is H) or methacryloyl chloride ($R^2$ is CH$_3$) in the presence of a base. Typical bases include tertiary amines. Examples of tertiary amines include triaklyamines (e.g., triethylamine, diethylmethylamine, dimethylisopropylamine, etc.), cyclic amines (e.g., 1,4-diazobicyclo[2.2.2]octane ("Dabco"), 1,5-diazabicyclo[4.3.0]non-5-ene ("DBN"), 1,8-diazabicyclo[5.4.0]undec-7-ene ("DBU"), etc.), aromatic amines (e.g., pyridine, N,N-dimethylaminopyridine, etc.). Reaction of the free hydroxy of the lysophospholipid with the acryloyl chloride converts the free hydroxyl group to an acrylate group, thus forming the phospholipid acrylate.

The synthesis of a phospholipid acrylate from a lysophospholipid may be performed with any lysophospholipid. Lysophospholipid cholines, however, are the most readily available starting materials. In an embodiment, a choline phospholipid acrylate may be formed from a lysophospholipid choline using the method depicted in FIG. 2. The obtained choline phospholipid acrylate may be converted to other phospholipid acrylates (e.g., serine phospholipid acrylates) using a transphosphatidylation enzyme (e.g., phospholipase D) as discussed previously (see, e.g., FIG. 1).

Figure 3:
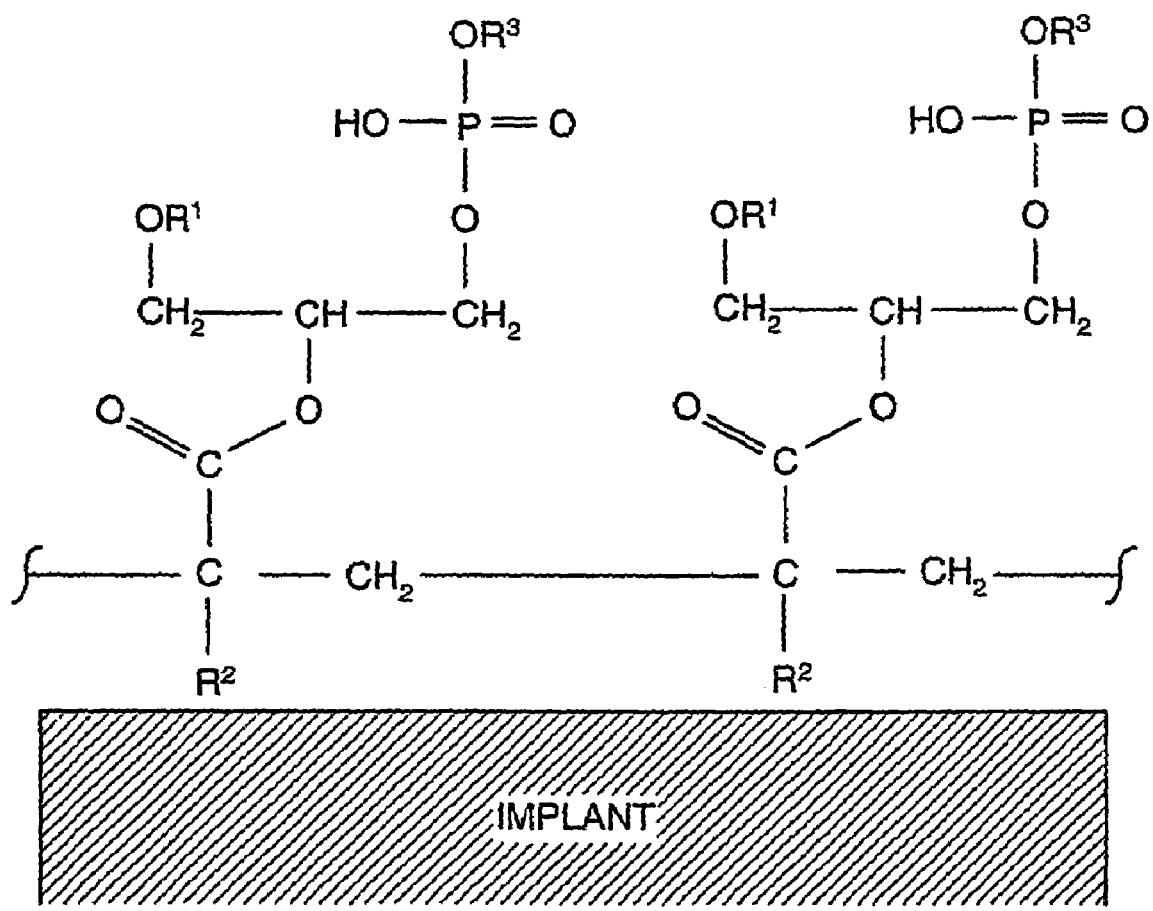
FIG. 3 a polymerized coating on an implant surface.

Phospholipid acrylates may be used to form polymeric coating on an implant. In an embodiment, the implant may be contacted with a coating composition. The coating composition includes a phospholipid acrylate and an initiator (e.g., a thermal initiator or a photoinitiator). The implant may be coated with the coating composition. The coating composition may be cured using suitable curing procedures (e.g., heating the implant or applying activating light to the coated implant). Curing of the coating composition produces a polymeric coating on the implant that includes phospholipid repeat units. A polymerized coating on an implant is depicted in FIG. 3, where $R^1$, $R^2$, and $R^3$ are as described before.

Any UV or thermal free radical initiator or mixture of initiators known to those skilled in the art of free radical polymerization can be used to initiate polymerization. Mixtures of the photoinitiators are sometimes preferred since they can in certain cases provide a more efficient production of radicals. Concentrations of the initiator in the polymerizable composition typically range from 0.1 to 5% by weight, although any amount can be used that provides the desired product.

It is known that the polymerization of ethylenically unsaturated monomers which can be polymerized by free radicals can be induced with the aid of radiation energy, such as ultraviolet and/or visible light. Photoinitiators which are transformed into a chemically reactive excited state either by direct absorption of light or by energy transfer from a sensitizer excited by a photochemical route are usually employed for this purpose. The free radicals which trigger off the polymerization are produced either by fragmentation of the excited photoinitiators or by reaction thereof with other molecules, for example hydrogen donors or electron donors, the free radicals which trigger off polymerization being formed from these other molecules.

One class of photoinitiators include 1,2 diketone initiators. Initiators of this type include adjacent carbonyl groups. 1,2-diketone initiators include aliphatic and aromatic 1,2-diketones. Examples of 1,2-diketone initiators include but are not limited to benzil, and benzil derivatives, aliphatic quinones (e.g., camphorquinone), and aromatic quinones (e.g. phenanthraquinone). 1,2 diketone photoinitiators are further described in U.S. Pat. No. 4,459,193 which is incorporated herein by reference.

Another class of photoinitiators are the acetophenone derived photoinitiators. Examples of acetophenone derived photoinitiators include but are not limited to, 2,2-di-sec-butoxyacetophenone, 2,2-diethoxyacetophenone, 2,2-diethoxy-2-phenyl-acetophenone, 2,2-dimethoxy-2-phenyl-acetophenone, benzoin methyl ether, and benzoin isobutyl ether. Other acetophenone derived photoinitiators are described in U.S. Pat. No. 3,715,293 which is incorporated herein by reference.

Another class of photoinitiators are the alpha-hydroxy ketone initiators. Examples of alpha-hydroxy ketone initiators include 2-hydroxy-2-methyl-1-phenylpropan-1-one and 1-hydroxycyclohexyl phenyl ketone. Examples of other alpha-hydroxy ketone initiators are described in U.S. Pat. No. 4,308,400 which is incorporated herein by reference.

Another class of photoinitiators includes the acylphosphine oxides. Examples of acylphosphine oxides include bis (2,6-dimethoxybenzoyl) (2,4,4 trimethyl phenyl) phosphine oxide and phenyl bis(2,4,6-trimethylbenzoyl) phosphine oxide, both commercially available from Ciba Additives in Tarrytown, N.Y. under the trade name of Irgacure 819. Other acylphosphine oxide initiators are described in detail in U.S. Pat. No. 5,721,292 which is incorporated herein by reference.

Other thermal and UV initiators include Other UV and thermal initiators include benzophenone, trimethylbenzophenone, isopropylthioxanthone, and ethyl 4-(dimethylamino)benzoate, benzoyl peroxide, acetyl peroxide, lauryl peroxide, azobisisobutyronitrile, t-butyl peracetate, cumyl peroxide, t-butyl peroxide, t-butyl hydroperoxide, bis(isopropyl)peroxydicarbonate, benzoin methyl ether, 2,2'-azobis(2, 4-dimethylvaleronitrile), tertiarybutyl peroctoate, phthalic peroxide, diethoxyacetophenone, and tertiarybutyl peroxypivalate, diethoxyacetophenone, phenothiazine, and diisopropylxanthogen disulfide.

Any of the above listed initiators may be used independently or in combination with each other. Additionally photosensitizers and coinitiators may be used with any of the above-referenced photoinitiators. Examples of coinitiators include but are not limited to reactive amine co-initiators commercially available from Sartomer Company under the trade names of CN-381, CN-383, CN-384, and CN-386, where these co-initiators are monoacrylic amines, diacrylic amines, or mixtures thereof. Other co-initiators include N-methyldiethanolamine (NMDEA), triethanolamine (TEA), ethyl-4-dimethylaminobenzoate (E4-DMAB), ethyl-2-dimethylaminobenzoate (E-2-DMAB), all commercially available from Aldrich Chemicals. Co-initiators which may also be used include n-butoxyethyl-4-dimethylamino benzoate, p-dimethyl amino benzaldehyde. Other co-initiators include N,N-dimethyl-p-toluidine, octyl-p-(dimethylamino) benzoate commercially available from The First Chemical Group of Pascagoula, Miss.

When photoinitiators are used in to polymerize the coating composition, the composition may be treated with activating light to induce polymerization. As used herein "activating light" means light that may affect a chemical change. Activating light may include ultraviolet light (e.g., light having a wavelength between about 150 nm to about 400 nm), actinic light, visible light or infrared light. Generally, any wavelength of light capable of affecting a chemical change may be classified as activating. Chemical changes may be manifested in a number of forms. A chemical change may include, but is not limited to, any chemical reaction that causes a polymerization to take place. Preferably the chemical change causes the formation of an initiator species within the coating composition, the initiator species being capable of initiating a chemical polymerization reaction.

In an embodiment, a photoinitiator composition for curing of phospholipid acrylates or methacrylates may include a photoinitiator and a photosensitizer. An example of a photoinitiator photosensitizer system uses camphorquinone as the photoinitiator and dimethyl acrylate-ethylmethyl acrylate ("DMA-EMA") as the photosensitizer. Activation of the polymerization reaction may be accomplished by applying ultraviolet light to the coating composition.

After polymerization the polymerized coating includes a plurality of phospholipid repeat units. The phospholipid repeat units may be converted to calcium-phospholipid-phosphates. In a general procedure the coated implant may be reacted with calcium chloride ($CaCl_2$) and ammonium hydrogenphosphate (($NH_4)_2HPO_4$). The reaction of the phospholipid groups with the calcium chloride and the ammonium hydrogenphosphate converts the phospholipid to calcium-phospholipid-phosphate complexes. The general procedure is the same as described earlier.

A hydroxyapatite coating may be deposited onto the polymeric coating. In an embodiment, the implant that includes the polymeric coating may be sterilized under an ultraviolet light source (e.g., 253.7 nm). The implant that includes the polymeric coating may be immersed in a natural biological fluid or a body fluid substitute (e.g., a solution that includes sodium chloride (NaCl), potassium hydrogenphosphate ($K_2HPO_4$), potassium dihydrogenphosphate ($KH_2PO_4$), magnesium chloride (MgCl), calcium chloride (CaCl), and potassium hydrogencarbonate ($KHCO_3$)). The implant may be immersed in the solution for a predetermined amount of time. The growth of hydroxyapatite on the surface of the implant is believed to be biomimetic.

Implants that may be coated in this manner may be formed from a variety of biocompatible materials. The most common materials include titanium. Titanium alloys may also be used as implant materials. An example of a titanium alloy is an allow of titanium alloyed with 6% aluminum and 4% vanadium. Other materials such as stainless steel, nickel-chromium alloys, nickel-chromium-cobalt alloys may be used. Implants may also be formed from biocompatible polymeric materials. Examples of polymeric materials include, but are not limited to, ultra high molecular weight polyethylene, polylactic acid, and polyglycolic acid.

Covalently Bound Phospholipids

In another embodiment, a coating layer for an implant may be covalently coupled to the implant. A phospholipid may be coupled to an implant via a linking group. In one embodiment, a phospholipid that includes a first linking group may be coupled to a second linking group of an implant. In this manner the phospholipid may be covalently bound to the implant surface. An example of a phospholipid that includes a covalent linker is a phospholipid carboxylate. A phospholipid carboxylate includes a free carboxylic acid or carboxylic acid derivative that may be used to covalently couple the phospholipid to the implant surface. An example of a phospholipid carboxylate is depicted as structure (V).

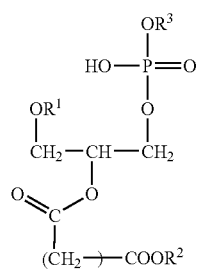

V where $R^1$ is H, $C_1$-$C_{24}$ alkyl, $C_2$-$C_{24}$ alkenyl, or $C(O)R^4$, where $R^4$ is $C_1$-$C_{24}$ alkyl or $C_2$-$C_{24}$ alkenyl;
where $R^2$ is H, alkyl, aryl, or benzyl;
where $R^3$ includes residues attached to the phosphate group. $R^3$ includes glycerol [$CH_2$—$CH(OH)$—$CH_2(OH)$]; choline [—$CH_2$—$CH_2$—$N(CH_3)_3^+$]; ethanolamine [—$CH_2$—$CH_2$—$NH_3^+$]; monomethylethanolamine [—$CH_2$—$CH_2$—$N(CH_3)H_2^+$];
dimethylethanolamine [—$CH_2$—$CH_2$—$N(CH_3)_2H^+$];
serine [—$CH_2$—$CH(NH_3)^+$—$CO_2^-$];
a carbohydrate

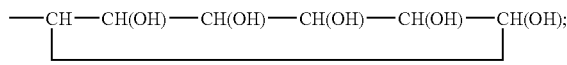

or
a diphosphatidylglycerol [—$CH_2$—$CH(OH)$—$CH_2$—O—$PO_3$—$CH_2$—$CH(OC(O)R^5)$—$CH_2$—$OC(O)R^6$], where $R^5$ and $R^6$ are each independently $C_1$-$C_{24}$ alkyl or $C_2$-$C_{24}$ alkenyl.

Figure 4A:
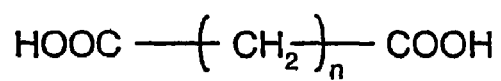
FIG. 4 depicts the synthesis of a phospholipid carboxylate.
Figure 4A:
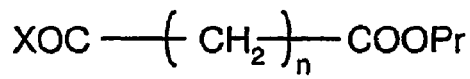
Figure 4B:
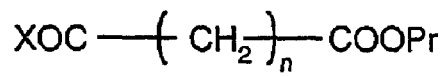
Figure 4B:
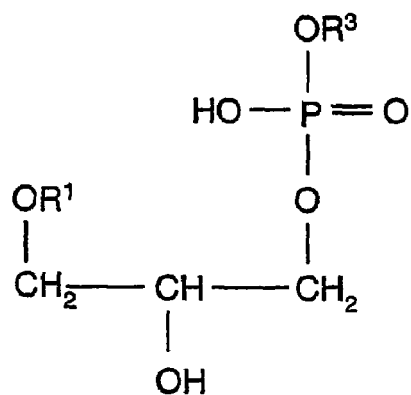
Figure 4B:
Figure 4B:
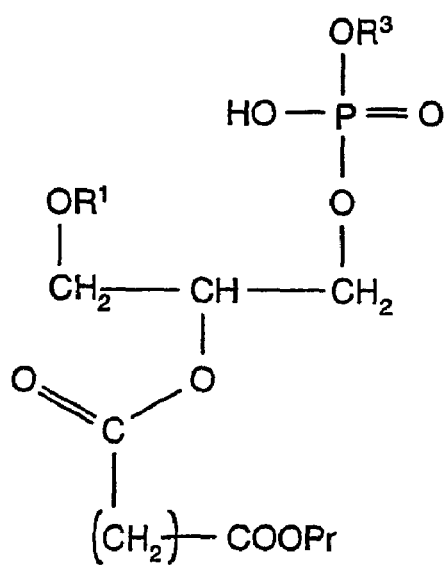

Phospholipid carboxylates may be formed from the reaction of a lysophospholipid with a dicarboxylic acid derivative as depicted in FIG. 4B. A lysophospholipid has the same structure as described previously. The dicarboxylic acid includes two carboxylic acid functional groups, a first carboxylic acid functional group (COOPr) may be relatively inert toward reaction with the lysophospholipid. The second carboxylic acid functional group (COX) may be reactive toward the lysophospholipid, particularly toward the free hydroxyl group. Dicarboxylic acid derivatives have the general structure (VI):

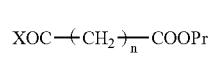

VI where Pr is a carboxylic acid protecting group, and X is a displaceable group and n is from 1 to 10. Protecting groups generally "protect" the carboxylic acid from subsequent reactions by converting the carboxylic acid group to a relatively unreactive derivative. At the appropriate time, typically after the reaction is complete, the protecting group may be removed. In this manner the reactivity of the carboxylic acid group may be restored at a later time. The conditions for removal of the protecting group may be chosen to not alter the chemical structure of other groups on the molecule. The carboxylic acid may be readily protected by forming an ester derivative of the carboxylic acid. Esterification of the carboxylic acid group may be accomplished by reacting the carboxylic acid with an alcohol in the presence of a catalyst (e.g., an acid). Common carboxylic acid protecting groups include, but are not limited to methyl, ethyl, t-butyl, and benzyl esters. Alky ester protecting groups may be removed by a hydrolysis reaction. Benzyl esters may be removed by hydrolysis or hydrogenation reactions. The displaceable group X, may be a halide, an ester, an imidazole, or an N-hydroxy-succinimide. All of these compounds may be produced by methods that are well known in the art.

The synthesis of a dicarboxylic acid derivative is depicted in FIG. 4A. A dicarboxylic acid as depicted in FIG. 4A (n is from 1 to 10) may be treated with a reagent to form a protecting group coupled to one of the carboxylic acid groups while the other carboxylic acid group is left unreacted. In an embodiment, the dicarboxylic acid may be reacted with an equimolar amount of benzyl chloride under basic conditions to form the monoprotected derivative VII

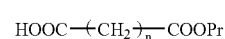

VII where Pr is $CH_2Ph$. Under these reaction conditions a mixture of monoester, diester, and unreacted dicarboxylic acid may be formed. The reaction products may be separated from each other using conventional techniques. The monoprotected compound may be converted into the dicarboxylic acid derivative by converting the unreacted carboxylic acid group to a reactive functional group. In one embodiment, the monoprotected compound may be treated with oxalyl chloride to convert the unreacted carboxylic acid group into an acid chloride. As depicted in FIG. 4A, Pr is $CH_2Ph$ and X is Cl for the product obtained.

The reactive dicarboxylic acid derivative may be reacted with a lysophospholipid as depicted in FIG. 4A. The free hydroxyl group of the lysophospholipid may displace the displaceable group X such that an ester bond is formed between the dicarboxylic acid and the hydroxyl group. In an embodiment, the dicarboxylic acid derivative (Pr is $CH_2Ph$ and X is Cl) may be reacted with the lysophospholipid, to produce a phospholipid carboxylate (Pr is $CH_2Ph$).

The synthesis of a phospholipid carboxylate from a lysophospholipid may be performed with any lysophospholipid. Lysophospholipid cholines, however, are the most readily available starting materials. In an embodiment, a choline phospholipid carboxylate ($R^3$ is choline) may be formed from a lysophospholipid choline using the method depicted in FIG. 4B. The obtained choline phospholipid carboxylate may be converted to other phospholipid carboxylates (e.g., serine phospholipid carboxylates) using a transphosphatidylation enzyme (e.g., phospholipase D) as discussed previously (see, e.g., FIG. 1). In order to couple serine phospholipid carboxylates to an implant, it may be necessary to protect the reactive functional groups (i.e., the amine and carboxylic acid groups) of serine. This may be readily accomplished by using N-t-Boc-serine-t-butyl ester instead of serine in a transphosphatidylation reaction. In this case, $R^3$ of the resulting product is N-t-Boc-serine-t-butyl ester [—$CH_2$—CH(N(H)tBu)—$CO_2$tBu].

To couple the phospholipid carboxylate to an implant, the implant surface may need to be prepared to create appropriate functional groups. In the case of metallic implants, the surface may be oxidized to create a surface of free hydroxyl groups. Metal implants include implants formed from titanium. Titanium alloys may also be used as implant materials. An example of a titanium alloy is an alloy of titanium alloyed with 6% aluminum and 4% vanadium. Other materials such as stainless steel, nickel-chromium alloys, nickel-chromium-cobalt alloys may be used. All of these metal implants may be treated with an oxidant to create free hydroxyls. A variety of methods may be used including treatment with oxygen, electrolysis of the materials, and acid treatment Acid oxidation of the implant may be accomplished by treating the implant with a combination of sulfuric acid and hydrogen peroxide. Details of this procedure may be obtained in the paper by Nanci et al. "Chemical modification of titanium surfaces for covalent attachment of biological molecules", *J. Biomedical Material Res.* 40(2), 3241-3245, 1998, which is incorporated herein by reference.

Figure 5:
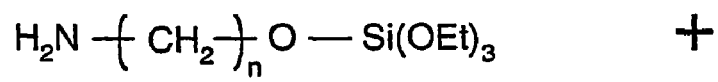
FIG. 5 depicts the synthesis of dicarboxylic acid linking groups.
Figure 5:
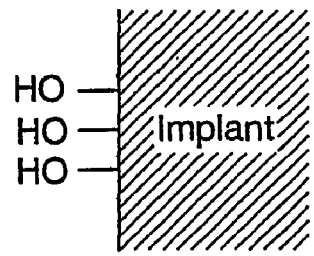
Figure 5:
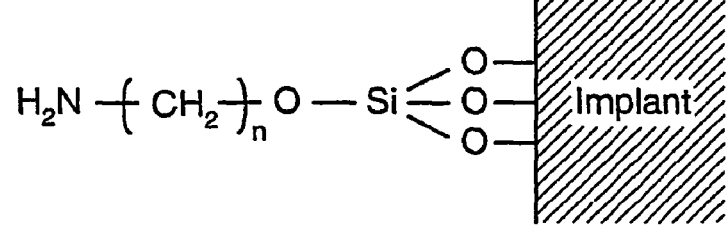

The oxidized implant surface may be further modified. A linking group may be coupled to the implant surface. The linking group may be used to couple the implant surface with the phospholipid carboxylate. Coupling of a linking group to the implant surface is depicted in FIG. 5. In one embodiment, a α-aminoalkylsilane (n is 1 to 10) may be used as a linker group. The ω-aminoalkylsilane may be reacted with the free hydroxyl groups of the implant surface to form a linkage unit coupled to the implant that has a terminal amino group.

Figure 6:
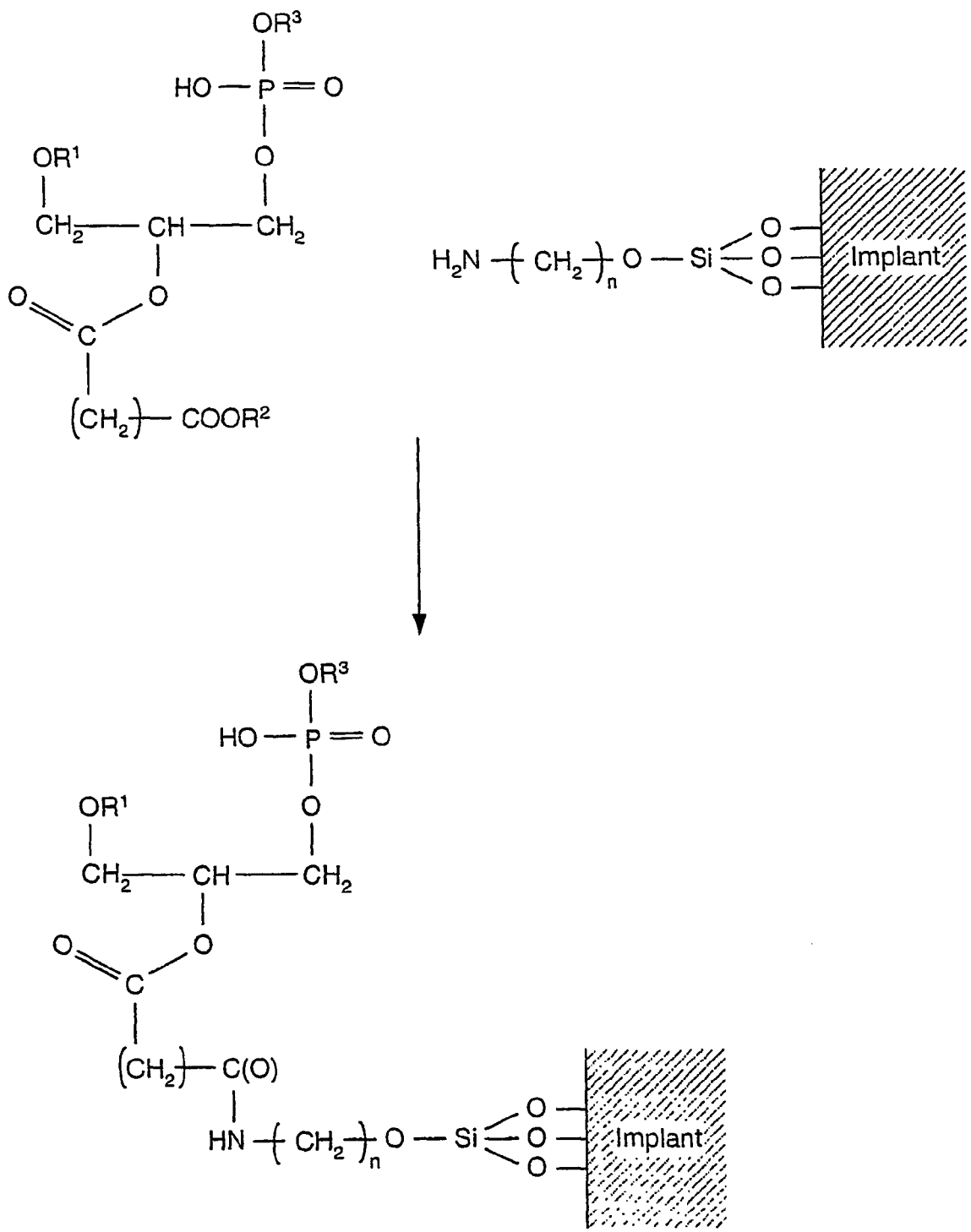
FIG. 6 depicts the covalent coupling of a phospholipid to an implant surface.

The treated implant and the phospholipid carboxylate may be coupled to each other as depicted in FIG. 6. The pendant carboxylic acid group of the phospholipid carboxylate is converted into a reactive derivative prior to coupling. After synthesis of the phospholipid carboxylate (See FIG. 4), the pendant carboxylic acid group is protected with a protecting group. The protecting group may be removed and to get the free carboxylic acid (see FIG. 6, $R^2$ is converted from Pr to H). In one embodiment, $R^2$ is $CH_2$Ph ("benzyl"). The benzyl protecting group may be removed under hydrogenation conditions to give the carboxylic acid ($R^2$ is H). Prior to coupling the carboxylic acid may be converted to a more reactive derivative. Examples of derivatives include acid halides and imidazole derivatives. In an embodiment, the carboxylic acid ($R^2$ is H) is treated with carbonyl diimidazole to form the imidazole derivative ($R^2$ is imidazole).

After activation of the phospholipid carboxylate, the phospholipid carboxylate is coupled with the amino terminus of the linker coupled to the implant as depicted in FIG. 6. Coupling may be accomplished using known methods. Further details concerning this method may be obtained in the paper by Ong et al. "Phospholipid Immobilization on Solid Surfaces" *Anal. Chem* 66, 782-792, 1994, which is incorporated herein by reference. In this manner a phospholipid may be covalently coupled to an implant surface. If serine based phospholipid are used, the t-Boc protecting groups may be removed after coupling by mild hydrolysis.

After coupling a plurality of phospholipid are covalently bound to the implant surface. The phospholipids may be converted to calcium-phospholipid-phosphates. In a general procedure the coated implant may be reacted with calcium chloride ($CaCl_2$) and ammonium hydrogenphosphate (($NH_4$)$_2HPO_4$). The reaction of the phospholipid groups with the calcium chloride and the ammonium hydrogenphosphate converts the phospholipid groups to calcium-phospholipid-phosphates. The general procedure is the same as described earlier.

A hydroxyapatite coating may be deposited onto the covalently linked coating. In an embodiment, the implant that includes the polymeric coating may be sterilized under an ultraviolet light source (e.g., 253.7 nm). The implant that includes the polymeric coating may be immersed in a natural biological fluid or a body fluid substitute (e.g., a solution that includes sodium chloride (NaCl), potassium hydrogenphosphate ($K_2HPO_4$), potassium dihydrogenphosphate ($KH_2PO_4$), magnesium chloride (MgCl), calcium chloride (CaCl), and potassium hydrogencarbonate ($KHCO_3$)). The implant may be immersed in the solution for a predetermined amount of time. The growth of hydroxyapatite on the surface of the implant is a self regulating process. The growth of the hydroxyapatite will stop, regardless of the time the implant remains in the solution.

Coupling of Bone Growth Promoting Proteins to an Implant

In an embodiment, bone growth promoting proteins may be coupled to an implant. Rapid osseointegration may be promoted by presence of growth factors, such as bone morphogenetic proteins ("BMPs"). Proteins may be coupled to an implant by a biodegradable spacer. The biodegradable spacer may be modified when the implant is inserted into a human body. The modification of the spacer may cause release of the protein into the vicinity of the implant. The release of bone growth factors may govern the bioactivity at the implant surface. It is believed that bone cell activity may be directly affected by bone growth factors (e.g., BMP-2) acting on immature mesenchymal-type cells to initiate bone induction through endochondral bone differentiation. In an embodiment, a bone morphogenetic protein ("BMP") may be coupled to an implant surface using a biodegradable spacer and a linker. A general representation of a protein coupled to an implant by a spacer and a linker is depicted as structure VIII.

VIII

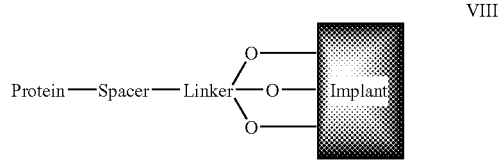

Prior to coupling a protein to an implant, the implant surface may need to be prepared to create appropriate functional groups. In the case of metallic implants, the surface may be oxidized to create a surface of free hydroxyl groups. Metal implants include implants formed from titanium. Titanium alloys may also be used as implant materials. An example of a titanium alloy is an allow of titanium alloyed with 6% aluminum and 4% vanadium. Other materials such as stainless steel, nickel-chromium alloys, nickel-chromium-cobalt alloys may be used. All of these metal implants may be treated with an oxidant to create free hydroxyls. A variety of methods may be used including treatment with oxygen, electrolysis of the materials, and acid treatment. Acid oxidation of the implant may be accomplished by treating the implant with a combination of sulfuric acid and hydrogen peroxide.

The oxidized implant surface may be further modified. A linking group may be coupled to the implant surface. The linking group may be used to couple the implant surface with the phospholipid carboxylate. Coupling of a linking group to the implant surface is depicted in FIG. 5. In one embodiment, a ω-aminoalkylsilane (n is 1 to 10) may be used as a linker group. The ω-aminoalkylsilane may be reacted with the free hydroxyl groups of the implant surface to form a linkage unit coupled to the implant that has a terminal amino group.

A biodegradable spacer group may also be coupled to the implant via the linking group. The biodegradable spacer group may serve two functions. First, the biodegradable spacer may allow the controlled release of the protein from the implant. The biodegradable spacer may be formed from a molecule that is slowly degraded when exposed to physiological conditions. Second, the spacer may serve as a "handle" by which the protein may be coupled to the linker. Any biodegradable spacer that meets these requirements may be used. Many types of compounds may be used as a biodegradable spacer. Examples of spacers include spacers that have the same monomeric functionality as poly-lactic acid, poly-glycolic acid and poly-hydroxy butyrate. Further examples of biodegradable spacers are described in the following references, all of which are incorporated herein by reference: Takaok et al. "Problems and Solutions in the Practical Use of Bone Morphogenetic Proteins", *J. Hard Tissue Biol.*, 5, 133-141, 1996; Oh et al. "Conjugation of drus to poly(dl-lactic-co-glycolic acid) for Controlled Release from Biodegradable Microsphere" *J. Controlled Release*, 57:269-280, 1999; and Thomas et al. "Symmetrical, Biodegradable Cross-linker Based on Lactic or Glycolic Acid: Preparation and Hydrolysis Rate Studied" *Book of Abstracts, 219th ACS National Meeting, San Francisco, Calif., Mar.* 26-30, 2000, ORGN-394.

Figure 7:
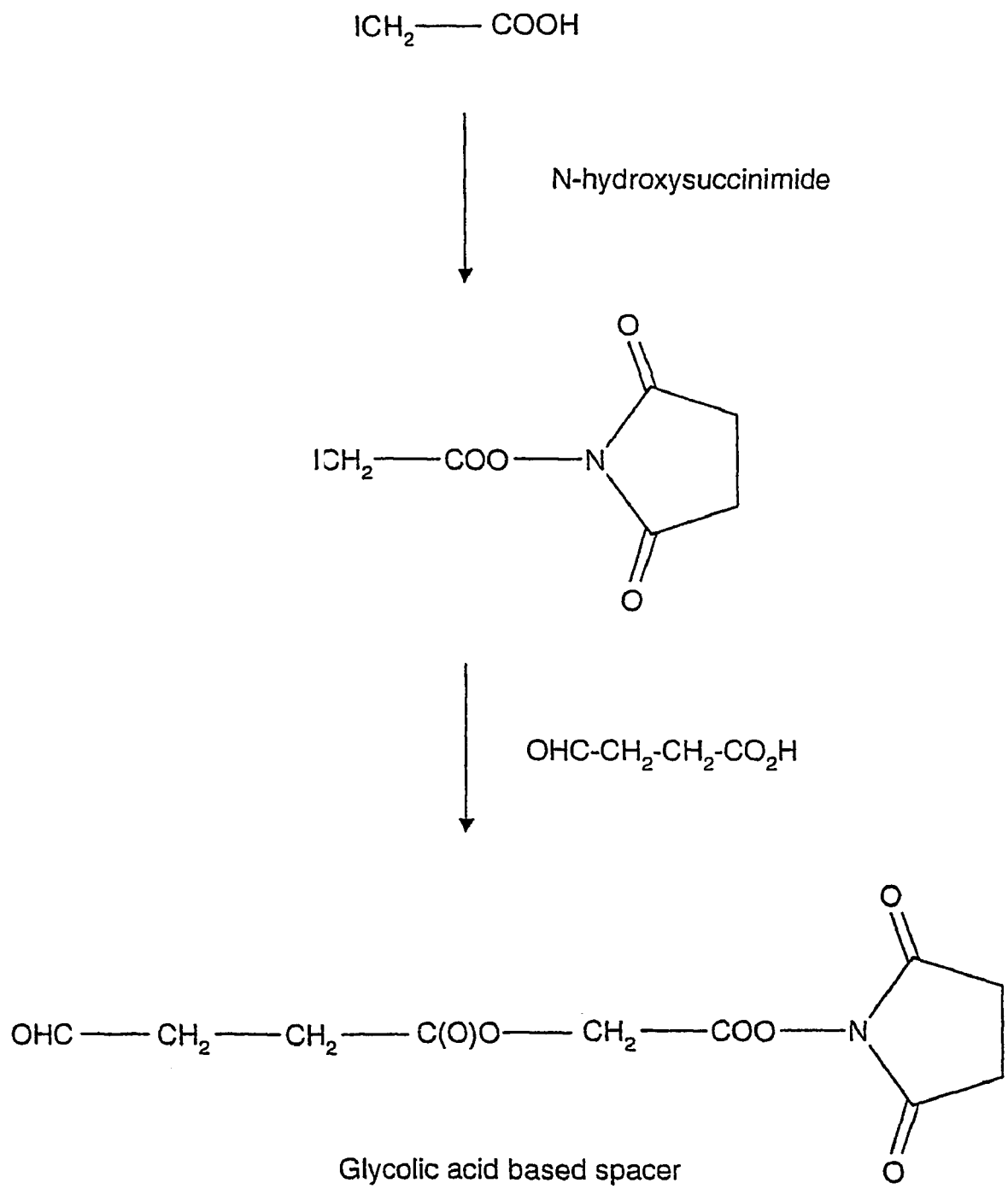
FIG. 7 depicts the synthesis of a biodegradable spacer.

The synthesis of a glycolic acid based spacer is depicted in FIG. 7. The spacer includes two functionalities, a functionality for coupling to the implant and a functionality for coupling to the protein. The spacer depicted in FIG. 7 includes a terminal aldehyde for coupling with an amino group of an implant and a terminal N-succinimide ester for coupling with an amino group of a protein molecule. In an embodiment, iodoacetic acid may be treated with N-hydroxysuccinimide to create a N-succinimide ester derivative. The reaction may be carried out in a non-polar solvent under anhydrous conditions. While iodoacetic acid is depicted, it should be understood that homologues of iodoacetic acid could be used in which the carboxylic acid functionality and the iodine are separated by additional carbon atoms (e.g., 3-iodopropionic acid).

The N-succinimide ester derivative may be further reacted with succinic-semialdehyde to produce the spacer as depicted in FIG. 7. The reaction of the N-succinimide ester derivative with succinic-semialdehyde may be performed under basic conditions in an anhydrous solvent.

The spacer may be coupled to the implant surface. In an embodiment, a linker is coupled to the implant surface, as depicted in FIG. 5, prior to coupling the spacer to the implant.

Figure 8:
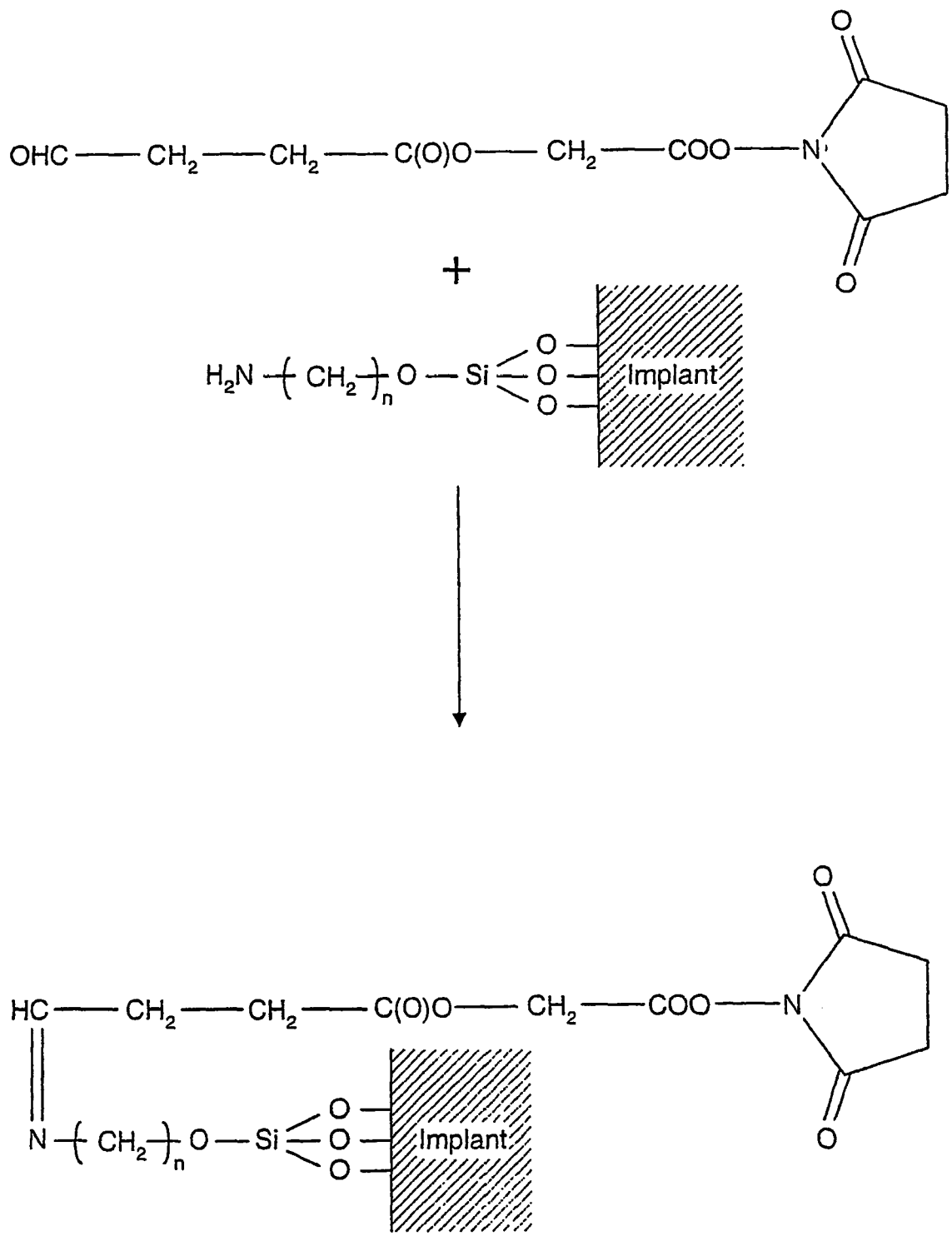
FIG. 8 depicts the coupling of a biodegradable spacer to an implant surface.

In some embodiments, the linker may include a terminal amino group. The reaction of an implant that includes a linker with a biodegradable spacer is depicted in FIG. 8. The terminal amine of the linker group may react with the terminal aldehyde of the spacer group to form an imine bond coupling the linker (and therefore the implant) to the spacer. The reaction may be carried out under acidic conditions in a nonaqueous polar solvent. The implant may be thoroughly washed with a solvent to remove any unreacted reagents after the reaction is completed.

Figure 9:
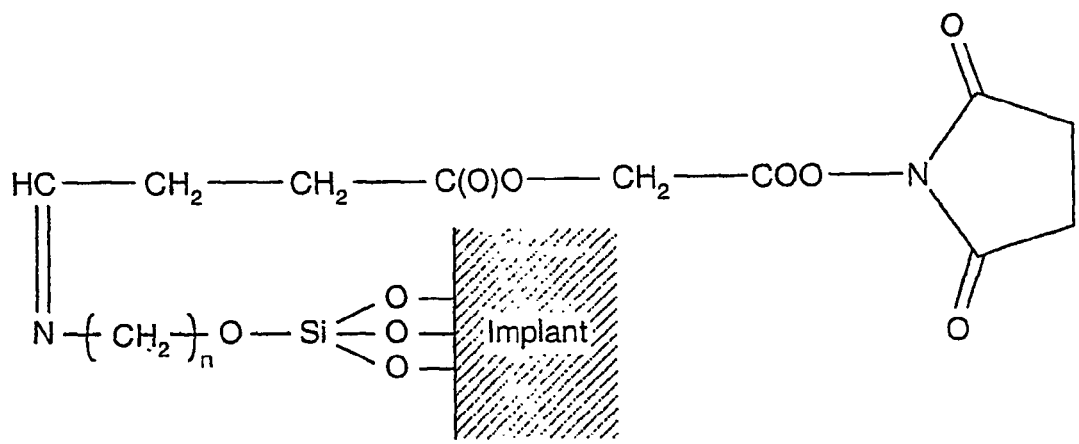
FIG. 9 depicts the coupling of a protein to an implant surface.
Figure 9:
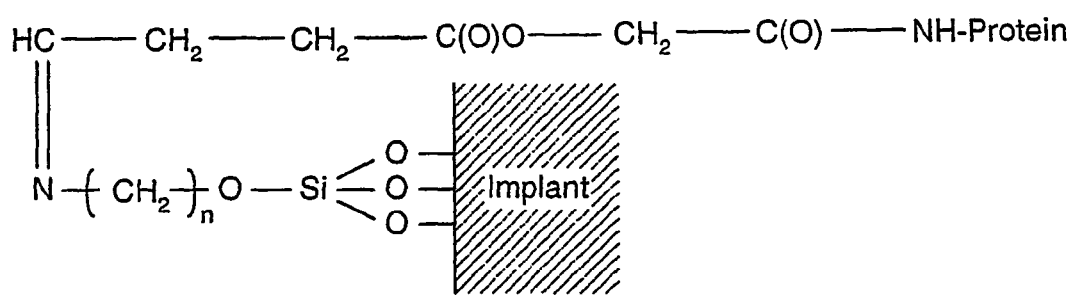

A bone growth promoting protein may be coupled to the spacer, and through the spacer and the linker, may be coupled to the implant The coupling of a protein to the spacer is depicted din FIG. 9. Coupling of the protein to the spacer may be accomplished in a buffered solution (pH between about 7 to 8). The amino group of the protein may displace the N-succinimide group to form an amide linkage between the spacer and the protein.

Any protein that promotes bone growth when released into the vicinity of a bone may be coupled in this manner to an implant. Among the most recognized bone growth promoting proteins are the bone morphogenetic proteins. Examples of bone morphogenetic proteins that may be used include, BMP-2, BMP-3, BMP-4, BMP-5, BMP-6, BMP-7, BMP-8, BMP-9, BMP-10, BMP-ll, BMP-15, and BMPY. Other proteins include growth differentiation factors such as GDF6, GDF7, GDF-9B, GDF10, and GDF11.

Coupling of Phospholipids and Bone Growth Promoting Proteins to an Implant Surface As previously discussed it is believed that the presence of a calcium-phospholipid-phosphate layer on the surface of an implant may enhance the formation of bone around the implant. It is further believed that the controlled release of bone growth promoting proteins may also promote enhanced growth of bone around the implant. In another embodiment, these two concepts may be combined to create an implant that includes calcium-phospholipid-phosphates and proteins coupled to an implant surface. A generalized structure (IX) depicts an embodiment an implant having both calcium-phospholipid-phosphates and bone growth promoting proteins.

IX

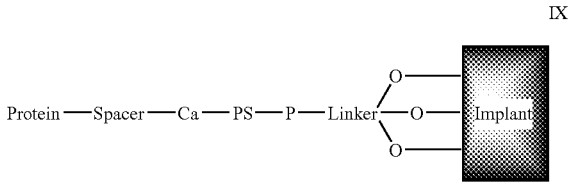

The implant includes a linker coupled to the implant surface. The linker may be used to form a bond between the implant and the calcium-phospholipid-phosphate (Ca—PS—P). The calcium phospholipid phosphate may be coupled to a biodegradable spacer. The spacer may be formed from a biodegradable material. A biodegradable spacer may allow the controlled release of the protein from the implant A bone growth promoting protein may be coupled to the spacer to produce the treated implant.

When implanted into a human, the implant may stimulate bone growth by two means. First, the bone growth promoting protein may be slowly released from the implant due to biodegradation of the spacer. Second, the presence of calcium-phospholipid-phosphate on the surface of the implant may induce further calcium phosphate deposition, enhance bone strength, and enhance osseointegration of the implant.

Coupling of the calcium-phospholipid-phosphate to the implant by use of a linker may be accomplished as has been previously described (See FIGS. 4-6 and accompanying description). The phospholipid group typically includes a reactive functional group as part of the phosphodiester group. Phosphodiester groups that include glycerol or inositol have hydroxyl groups that may be coupled to a spacer group. Phosphodiester groups that include serine or ethanol amine include reactive amine groups that may be coupled to a spacer group.

A biodegradable spacer molecule may be coupled to the phospholipid group. The spacer molecule may be the same spacer as has been previously described (See FIG. 7 and accompanying description). When an amine containing phosphodiester group is coupled with the spacer, two possible reaction products may result. Product (X) represents the reaction product of a serine ($R^6$ is COOH) or ethanolamine ($R^6$ is H) phosphodiester group with the aldehyde portion of the spacer to form a imine linkage between the phosphodiester and the spacer. $R^7$ is N-hydroxysuccinimide.

X

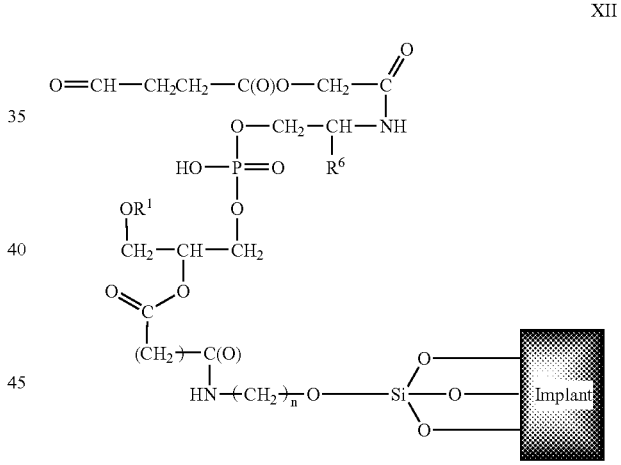

The carboxylic acid group of the spacer may be deprotected and serve as a handle to couple a bone growth promoting protein to the implant.

The compound (X) may be obtained by reaction of the spacer group with the phosphodiester group of the phospholipid coupled to the implant. The protein may be coupled to the implant in a subsequent reaction to give the desired treated implant (XI).

XI

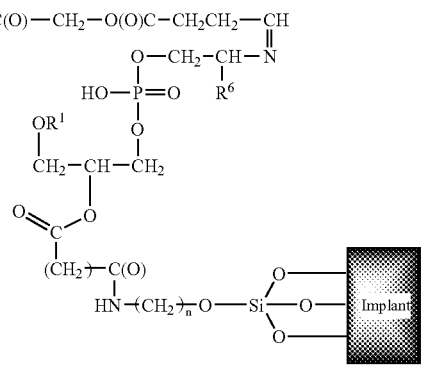

In another embodiment, the formation of product (XI) may be accomplished by the reaction of the implant (with the phospholipid coupled to the surface), the spacer, and the protein. This reaction may allow coupling of the spacer and protein to the implant at the same time.

The reaction of the spacer with the phosphodiester group may produce alternate products. In an embodiment, the carboxylic acid portion of the spacer may react with the phosphodiester group to produce product (XII).

XII

The compound (XII) may be obtained by reaction of the spacer group with the phosphodiester group of the phospholipid coupled to the implant The protein may be coupled to the implant in a subsequent reaction to give the desired treated implant (XIII). In another embodiment, the formation of product (XI) may be accomplished by the reaction of the implant (with the phospholipid coupled to the surface), the spacer, and the protein. This reaction may allow coupling of the spacer and protein to the implant at the same time.

In another embodiment, the formation of products (XI) and (XIII) may be accomplished by the reaction of the implant (with the phospholipid coupled to the surface), the spacer, and the protein. This reaction may allow coupling of the spacer and protein to the implant at the same time. The ratio of products may be determined by the kinetics of imine versus amide formation between the spacer and the phosphodiester groups.

XIII

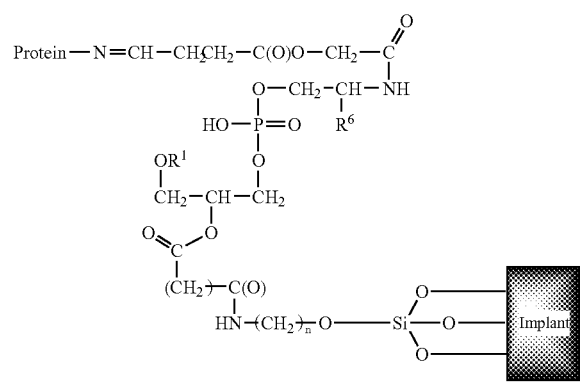

A plurality of phospholipid are covalently bound to the implant surface. The phospholipids may be converted to calcium-phospholipid-phosphates. In a general procedure the coated implant may be reacted with calcium chloride ($CaCl_2$) and ammonium hydrogenphosphate (($NH_4$)$_2HPO_4$). The reaction of the phospholipid groups with the calcium chloride and the ammonium hydrogenphosphate converts the phospholipid groups to calcium-phospholipid-phosphates. The general procedure is the same as described earlier.

A hydroxyapatite coating may also be deposited onto the covalently linked coating. In an embodiment, the implant that includes the polymeric coating may be sterilized under an ultraviolet light source (e.g., 253.7 nm). The implant that includes the polymeric coating may be immersed in a natural biological fluid or a body fluid substitute (e.g., a solution that includes sodium chloride (NaCl), potassium hydrogenphosphate ($K_2HPO_4$), potassium dihydrogenphosphate ($KH_2PO_4$), magnesium chloride (MgCl), calcium chloride (CaCl), and potassium hydrogencarbonate ($KHCO_3$)). The implant may be immersed in the solution for a predetermined amount of time. The growth of hydroxyapatite on the surface of the implant is believed to be biomimetic.

Testing of Coated Implanted Materials

The amount of calcium-phospholipid-phosphate adsorbed on the implant may be quantitated. After the calcium-phospholipid-phosphate complex is applied to the implant surface and the excess complex is washed off, a coating of the applied material still remains on the implant surfaces. The coating may be removed by rinsing the implant with a mixture of chloroform, methanol and 0.1N HCl (1:2:0.8). The rinse solution includes the calcium-phospholipid-phosphate complex removed from the implant. The recovered calcium-phospholipid-phosphate is reacted with pentafluorobenzoic anhydride or trifluoroacetic acid to convert the phospholipid to a 1,2-diacyl-sn-glycerol pentafluorobenzoate or trifluoroacetate. The resulting pentafluorobenzoates may be quantitated using gas chromatography/mass spectrometry to determine the amount of calcium-phospholipid-phosphate adsorbed onto the implant Further details may be obtained from the paper by Satsangi et al. "A Novel Method for the Analysis of Platelet Activating Factor: Direct Derivatization of Glycerophospholipids", *J. Lipid Res.* 30, 929-937, 1989, which is incorporated herein by reference.

The ability of the coated implant to promote bone growth may be assayed using cell culture testing procedures. Cell culture tests, may examine cell proliferation, collagen and total protein production, alkaline phosphatase specific activity, and 1,25(OH)$_2$ vitamin $D_3$ stimulated osteocalcin production, as well as for mineralized nodule formation. Sterilized samples of coated implants may be placed at the bottom of a well of a 24-well plate. A HEPM cell suspension (osteoblast progenitor cell line) is seeded into each well at $1.5 \times 10^4$ cells/$cm^2$. Alpha modified Eagle's medium containing 7% fetal bovine serum, 1% antibiotic-antimycotic solution, 50 µg/ml ascorbic acid, and 4 mM β-glycerophosphate may be used. The cultures are maintained in a humidified 95% air, 5% $CO_2$ atmosphere at 37° C. The medium may be changed the day after seeding to remove nonadherent cells. The cultures may be assayed at 0, 3, 7, 14, 21, and. 25 days.

Cell proliferation of the assayed cultures may be determined. Twenty-four hours prior to designated times of experimentation, the medium is changed to serum-free medium. Three hours prior to harvest, the cells are pulsed with 0.2 µCi/ml[$^3$H]-thymidine. Cells are harvested after washing with phosphate buffered solution (PBS) to remove unincorporated extracellular label followed by washes with 10% trichloroacetic acid (TCA). The cell layers are solubilized in 1 N NaOH and aliquots of the solubilized cells may be neutralized with hydrochloric acid (HCl) and then mixed with liquid scintillant and counted in a scintillation spectrometer.

Collagen production may also be assayed. Three hours prior to harvest, 10 µCi/ml of [$^3$H]-proline is added to the wells to label the cells. At the end of the labeling period, the unincorporated label is washed away with PBS and protein precipitated with 10% TCA. The precipitated protein may be solubilized in 1 N NaOH. Aliquots of the solubilized protein are neutralized with HCl, and the sample incubated with pure bacterial collagenase in buffered calcium-containing solution; followed by digestion at 37° C. for 90 min. Digestion is terminated by transferring the samples to an ice-cold bath followed by the addition of a solution of bovine-serum albumin (BSA) and 10% TCA to re-precipitate proteins. The precipitated protein aliquots of the supernatant containing collagenase-digested protein (CDP) is pelleted and mixed with liquid scintillant and counted in a scintillation spectrometer. The pellet is dissolved in NaOH, neutralized and an aliquot counted in liquid scintillant as non-collagen protein (NCP). The percent collagen synthesis may be calculated as follows:

$$\% \text{ Collagen} = \frac{CDP}{(5.4 \times NCP) + CDP} \times 100$$

Protein Production may also be determined. Protein production may be determined using the Pierce BCA protein assay (Pierce, Rockford, Ill.). At harvest, the medium from the cell culture is removed and discarded. The cell layers are lysed with 1 ml of triton X-100 (0.2%). A 30 µl aliquot of the cell lysate is added to 200 µl of BCA working reagent in a 96 well culture plate and incubated for 30 minutes at 37° C. Absorbance may be measured at 600 nm using a microplate reader.

Alkaline phosphatase specific activity may be assayed. A 50 μl aliquot of the same cell lysate used for protein determination is added to 50 μl of working reagent in a 96 well culture plate and incubated for 1 hour at 37° C. The working reagent includes 1.5 M 2-amino-2 methyl-1-propanol, 20 mM p-nitrophenyl phosphate and 1 mM magnesium chloride (1:1:1). The reaction is stopped using 100 μl of 1 N sodium hydroxide and the absorbance read at 410 nm using a microplate reader. Alkaline phosphatase specific activity may be calculated using the previously determined protein values.

Osteocalcin production may also be assayed. At the experimental time point, media is removed and replaced with fresh media alone, or media containing $2.5 \times 10^{-9}$ M 1,25 (OH)$_2$ vitamin D$_3$. After 24 hours, the media may be replaced again with either media alone or the 1,25 (OH)$_2$ vitamin D$_3$ containing media. After 48 hours, the media is collected and frozen at $-20°$ C. until assay. The samples are lyophilized using a speed-vac. The 1,25 (OH)$_2$ vitamin D$_3$ stimulated osteocalcin production may be measured using commercially available rat osteocalcin radioimmunoassay reagents (Biomedical Technologies, MA). At the day of the assay, the samples are reconstituted to 1/5 of the original starting volume in a tris-saline working buffer. The samples (50 μl) or rat osteocalcin standard (50 μl) are added to a pool of rat osteocalcin antiserum (100 μl), normal rabbit serum (100 μl), $^{125}$I rat osteocalcin radioactive tracer (100 μl) and tris-saline buffer (200 μl). These are vortexed and incubated overnight at room temperature on an orbital platform shaker at 80 rpm. On the second day, 100 μl of the second antibody (goat anti-rabbit IgG) and 100 μl of the polyethylene glycol solution is added, vortexed, and incubated at room temperature for 2 hours on an orbital shaker at 80 rpm. The tubes are centrifuged at 1800 rpm at 4° C. for 30 minutes. The supernatant is aspirated and the pellets counted in a gamma spectrometer for 2 minutes.

Mineralized nodule area may be determined using computer-assisted image analysis of cultures in which the nodules are viewed under fluorescent light. Because the cultures are grown on calcium-phospholipid-phosphate containing substrates, traditional staining methods using Von Kossa stain are not possible. Therefore, cultures are treated with procion brilliant red dye which labels proteins associated with mineralizing matrix. The compound is non toxic to cells and its presence in the culture medium should not alter the normal metabolic activity of the cells. When viewed under fluorescent light, this dye yields a bright red color which is easily imaged. The area of the culture that fluoresces will be expressed as a percentage of the total culture area to give a measure of the mineralization capacity each cell culture system.

While this invention has been described with references to various illustrative embodiments, the description is not intended to be construed in a limiting sense. Various modifications and combinations of the illustrative embodiments as well as other embodiments of the invention, will be apparent to persons skilled in the art upon reference to the description. It is, therefore, intended that the appended claims encompass any such modifications or embodiments.

What is claimed is:

1. An implant configured to be implanted in a human, comprising an implant surface coated with a coating, wherein the coating has the structure:

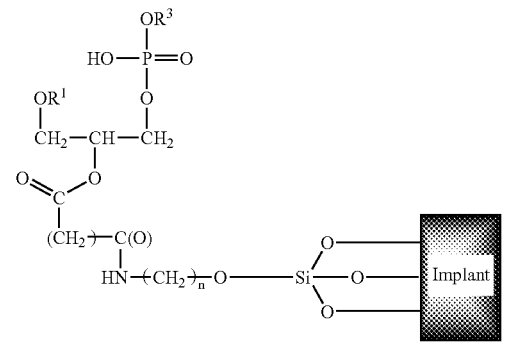

wherein $R^1$ is H, $C_1$-$C_{24}$ alkyl, $C_2$-$C_{24}$ alkenyl, or $C(O)R^4$, where $R^4$ is $C_1$-$C_{24}$ alkyl or $C_2$-$C_{24}$ alkenyl;

where $R^3$ is —CH$_2$—CH(OH)—CH$_2$(OH); —CH$_2$—CH$_2$—N(CH$_3$)$_3^+$; —CH$_2$—CH$_2$—NH$_3^+$; —CH$_2$—CH$_2$—N(CH$_3$)H$_2^+$; —CH$_2$—CH$_2$—N(CH$_3$)$_2$H$^+$; —CH$_2$—CH(NH$_3$)$^+$—CO$_2^-$;

—CH—CH(OH)—CH(OH)—CH(OH)—CH(OH)—CH(OH); or or
—CH$_2$—CH(OH)—CH$_2$—O—PO$_3$—CH$_2$—CH(OC(O)R$^5$)—CH$_2$—OC(O)R$^6$
where $R^5$ and $R^6$ are each independently $C_1$-$C_{24}$ alkyl or $C_2$-$C_{24}$ alkenyl; and
where n is 1 to 10.

2. The implant of claim 1, wherein $R^1$ is $C(O)R^4$, where $R^4$ is $C_1$-$C_{24}$ alkyl or $C_2$-$C_{24}$ alkenyl, and wherein $R^3$ is —CH$_2$—CH(OH)—CH$_2$(OH); —CH$_2$—CH(NH$_3$)$^+$—CO$_2^-$;

—CH—CH(OH)—CH(OH)—CH(OH)—CH(OH)—CH(OH); or or
—CH$_2$—CH(OH)—CH$_2$—O—PO$_3$—CH$_2$—CH(OC(O)R$^5$)—CH$_2$—OC(O)R$^6$
where $R^5$ and $R^6$ are each independently $C_1$-$C_{24}$ alkyl or $C_2$-$C_{24}$ alkenyl.

3. The implant of claim 1, wherein the implant comprises titanium.

4. The implant of claim 1, wherein the implant comprises a titanium alloy, the titanium alloy comprising titanium, aluminum, and vanadium.

5. The implant of claim 1, wherein the implant comprises biocompatible stainless steel, nickel-chromium alloys or nickel-chromium-cobalt alloys.

6. The implant of claim 1, wherein the implant is an orthopedic implant.

7. The implant of claim 1, wherein the implant is a dental implant.

* * * * *